(12) United States Patent
Chang

(10) Patent No.: US 7,243,652 B2
(45) Date of Patent: Jul. 17, 2007

(54) RESPIRATOR MASK

(75) Inventor: Eric Chang, Taichung Hsien (TW)

(73) Assignee: Hsiner Co., Ltd., Taichung Hsien (TW)

( * ) Notice: Subject to any disclaimer, the term of this patent is extended or adjusted under 35 U.S.C. 154(b) by 344 days.

(21) Appl. No.: 10/922,922

(22) Filed: Aug. 23, 2004

(65) Prior Publication Data

US 2006/0081240 A1   Apr. 20, 2006

(51) Int. Cl.
*A62B 18/08* (2006.01)
*A62B 18/02* (2006.01)

(52) U.S. Cl. .............................. 128/206.26; 128/206.28

(58) Field of Classification Search ........... 128/206.28, 128/206.26, 206.12, 203.29, 205.25, 201.23, 128/857, 863, 200.24

See application file for complete search history.

(56) References Cited

U.S. PATENT DOCUMENTS 6,651,661 B2 * 11/2003 Matioc .................. 128/205.25
6,860,268 B2 * 3/2005 Bohn et al. ............. 128/206.21
2005/0005931 A1 * 1/2005 Doane et al. .......... 128/200.24

* cited by examiner

*Primary Examiner*—Justine R. Yu
*Assistant Examiner*—Annette Dixon
(74) *Attorney, Agent, or Firm*—Pillsbury Winthrop Shaw Pittman, LLP

(57) ABSTRACT

A respirator mask includes an inflatable cuff, a gas-guiding member, and an inflating valve. The inflatable cuff has an inner wall surface confining an air chamber, and a gas inlet unit having a hollow protrusion projecting into the air chamber from the inner wall surface. The hollow protrusion has an innermost end wall spaced apart from the inner wall surface and a through hole formed in the innermost end wall. The hollow protrusion is formed as one-piece with the inner wall surface. The gas-guiding member has an annular connecting edge portion which is connected to the inflatable cuff and which has a hollow seat aligned with the hollow protrusion. The hollow seat has a through hole communicated with the through hole of the hollow protrusion. The inflating valve is mounted in the hollow seat.

5 Claims, 6 Drawing Sheets

RESPIRATOR MASK

BACKGROUND OF THE INVENTION

1. Field of the Invention

The invention relates to a mask, more particularly to a respirator mask, which can be fabricated with relative ease.

2. Description of the Related Art

Referring to FIGS. 1 and 2, a conventional respirator mask includes an inflatable cuff 1, a gas-guiding member 2 mounted on the inflatable cuff 1, and an inflating valve 3 mounted on the inflatable cuff 1 for inflating the cuff 1.

The inflatable cuff 1 is made in a form of an annular hollow body by blow molding or by rotational molding, and has a broad mouth covering portion 11, a tapered nose covering portion 12, and an inflating hole 13 corresponding to the inflating valve 3. Additionally, the inflatable cuff 1 has an annular connecting portion 14, which is relatively thick due to being made by rotational molding. If the inflatable cuff 1 is made by blow molding, the thickness of the annular connecting portion 14 is reduced.

The gas-guiding member 2 has an annular connecting edge portion 21 connected to the annular connecting portion 14 of the inflatable cuff 1, a hose connecting tube 23, a skirt member 22 extending from the annular connecting portion 21 to the hose connecting tube 23, and a hollow seat 24 aligned with the inflating-hole 13. The hose connecting tube 23 is used for connecting a tube (not shown) thereto so as to introduce gas, such as oxygen, into the mask via the tube for respiration of a patient. The hollow seat 24 has a hollow seat body 241 for mounting the inflating valve 3 therein, and a through hole 242.

The inflating valve 3 is mounted on the hollow seat 24, and is aligned and communicates with the inflating hole 13 for inflating the inflatable cuff 1 therethrough.

In use, the inflatable cuff 1 is inflated by introducing air through the inflating valve 3 from a inflating device (not shown). Therefore, the inflatable cuff 1 of the mask can cover the mouth and the nose of the patient closely.

However, the inflating hole 13 can not be preformed by blow molding or by rotational molding because it is not permissible to have any hole for communicating to the ambient environment during the blow molding or the rotational molding. Therefore, the inflating hole 13 is formed after the inflatable cuff 1 is molded. Furthermore, the gas-guiding member 2 is usually connected to the inflatable cuff 1 using an adhesive. In order to avoid the inflating hole 13 from being blocked by the adhesive, the inflating hole 13 is formed after the gas-guiding member 2 is connected to the inflatable cuff 1. However, the inflating hole 13 can not be formed by cutting the inflatable cuff 1 formed by rotational molding directly due to the relatively large thickness thereof. As for the inflatable cuff 1 formed by blow molding, although the thickness thereof is relatively small, the surface of the inflatable cuff 1 to be formed with the inflating hole 13 is a continuous surface. Hence, it is not easy to control the size of the inflating hole 13 properly by cutting. If the inflating hole 13 is too large, the inflatable cuff 1 is easily damaged due to breaking or deformation. On the other hand, if the inflating hole 13 is too small, it may get blocked during use, which can lead to insufficient inflation of the inflatable cuff 1. Therefore, the inflating hole 13 is usually formed by drilling in the prior art. However, the adhesive between the inflatable cuff 1 and the gas-guiding member 2 is liable to overflow therefrom and to cure on the surface of the inflatable cuff 1, which can make drilling of the inflating hole 13 relatively difficult to conduct.

SUMMARY OF THE INVENTION

Therefore, the object of the present invention is to provide a respirator mask which can be fabricated with relative ease.

Accordingly, the respirator mask of this invention includes an inflatable cuff, a gas-guiding member, and an inflating valve. The inflatable cuff has an inner wall surface confining an air chamber, and a gas inlet unit having a hollow protrusion projecting into the air chamber from the inner wall surface. The hollow protrusion has an innermost end wall spaced apart from the inner wall surface and a through hole formed in the innermost end wall. The hollow protrusion is formed as one-piece with the inner wall surface. The gas-guiding member has an annular connecting edge portion which is connected to the inflatable cuff and which has a hollow seat aligned with the hollow protrusion. The hollow seat has a through hole communicated with the through hole of the hollow protrusion. The inflating valve is mounted in the hollow seat.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
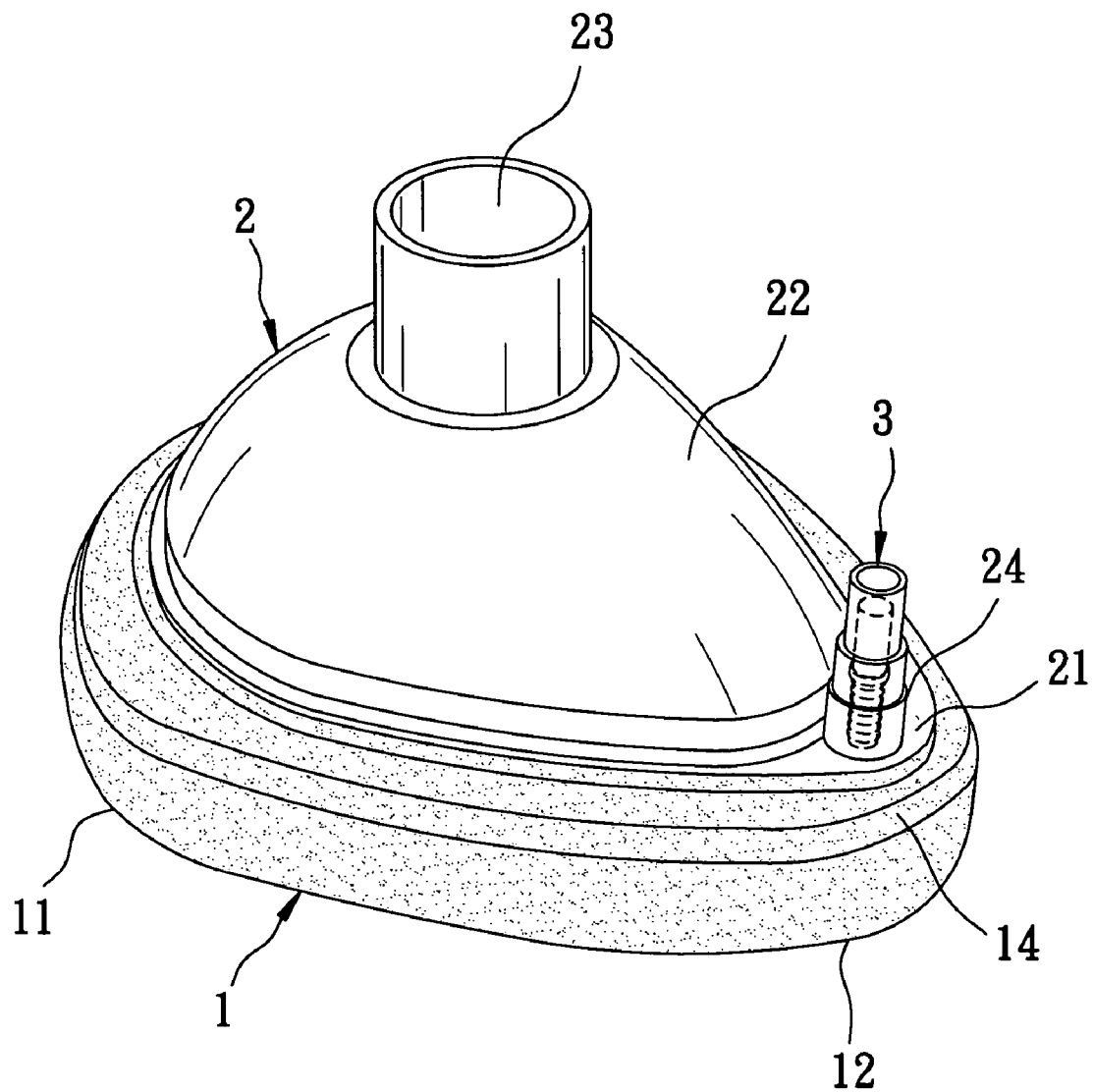
FIG. 1 is a perspective view of a conventional respirator mask.
Figure 2:
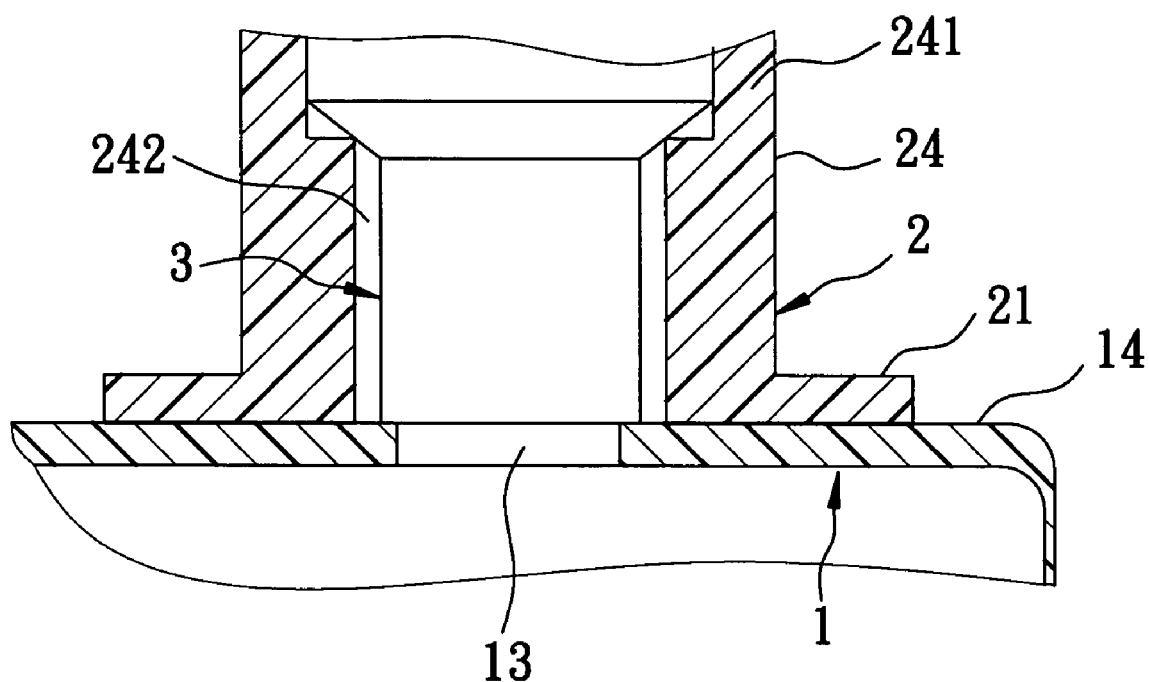
FIG. 2 is a fragmentary sectional view of the conventional respirator mask.

Before the present invention is described in greater detail, it should be noted that like elements are denoted by the same reference numerals throughout the disclosure.

Figure 3:
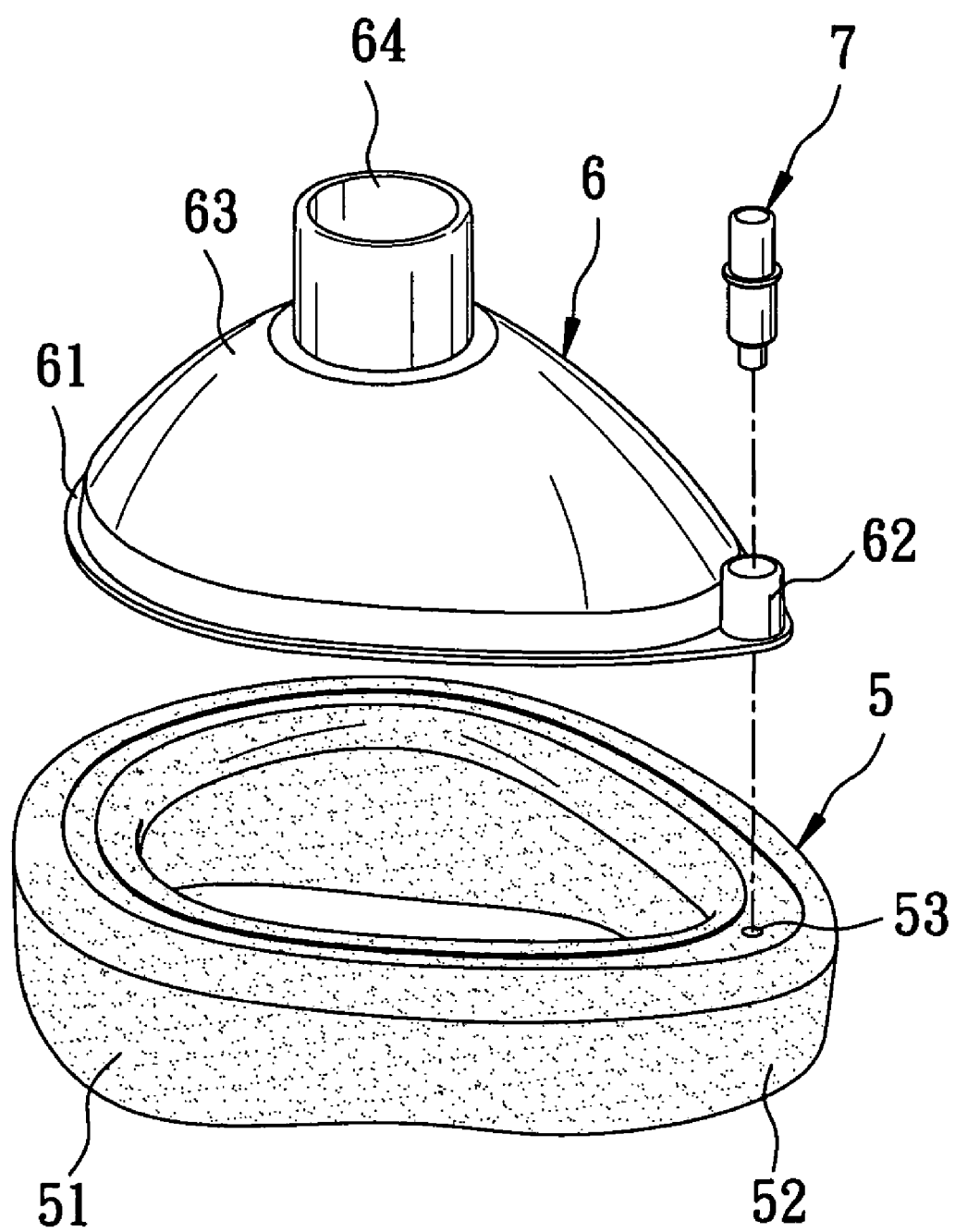
FIG. 3 is an exploded perspective view of a first preferred embodiment of a respirator mask according to this invention.
Figure 4:
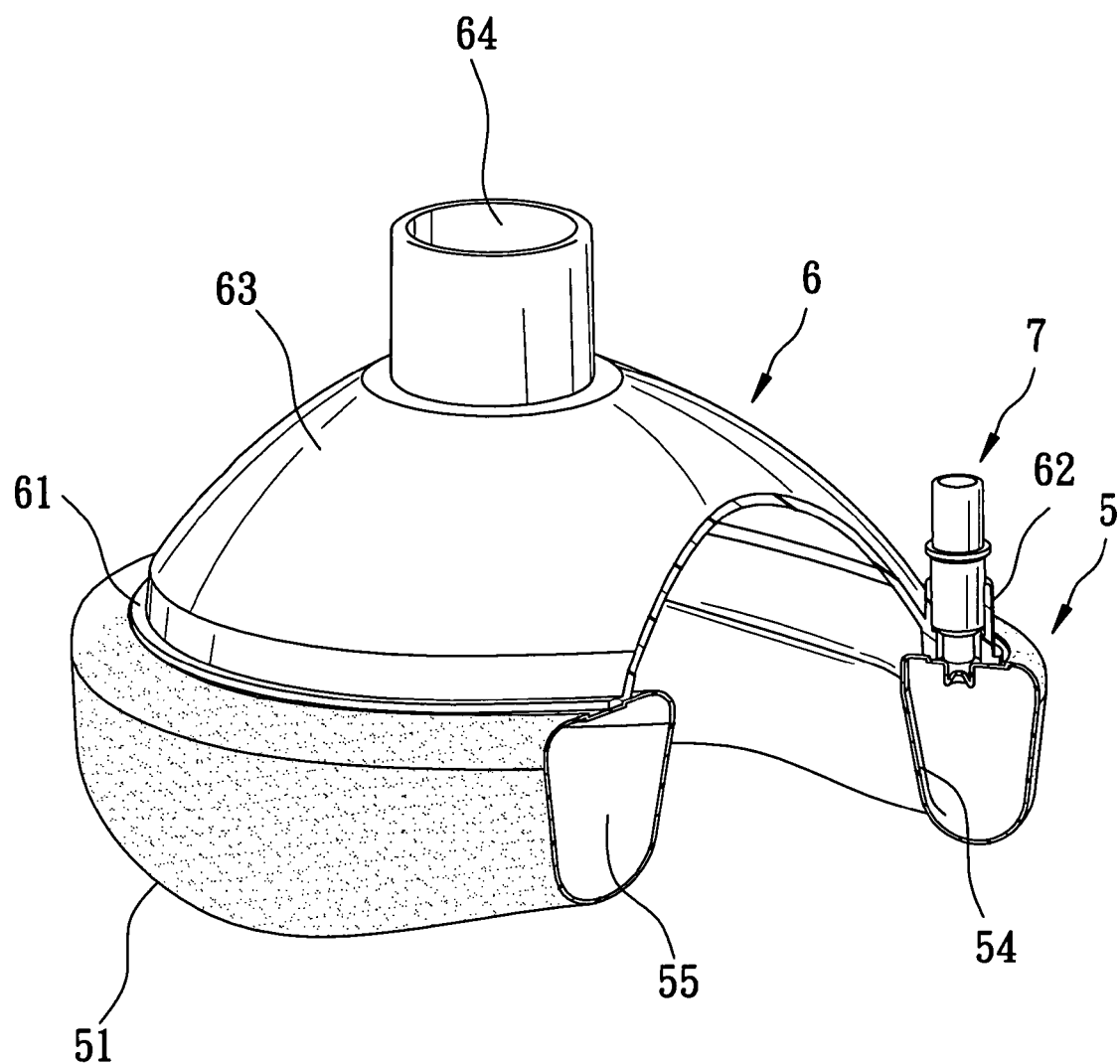
FIG. 4 is a partly cutaway perspective view of the first preferred embodiment.
Figure 5:
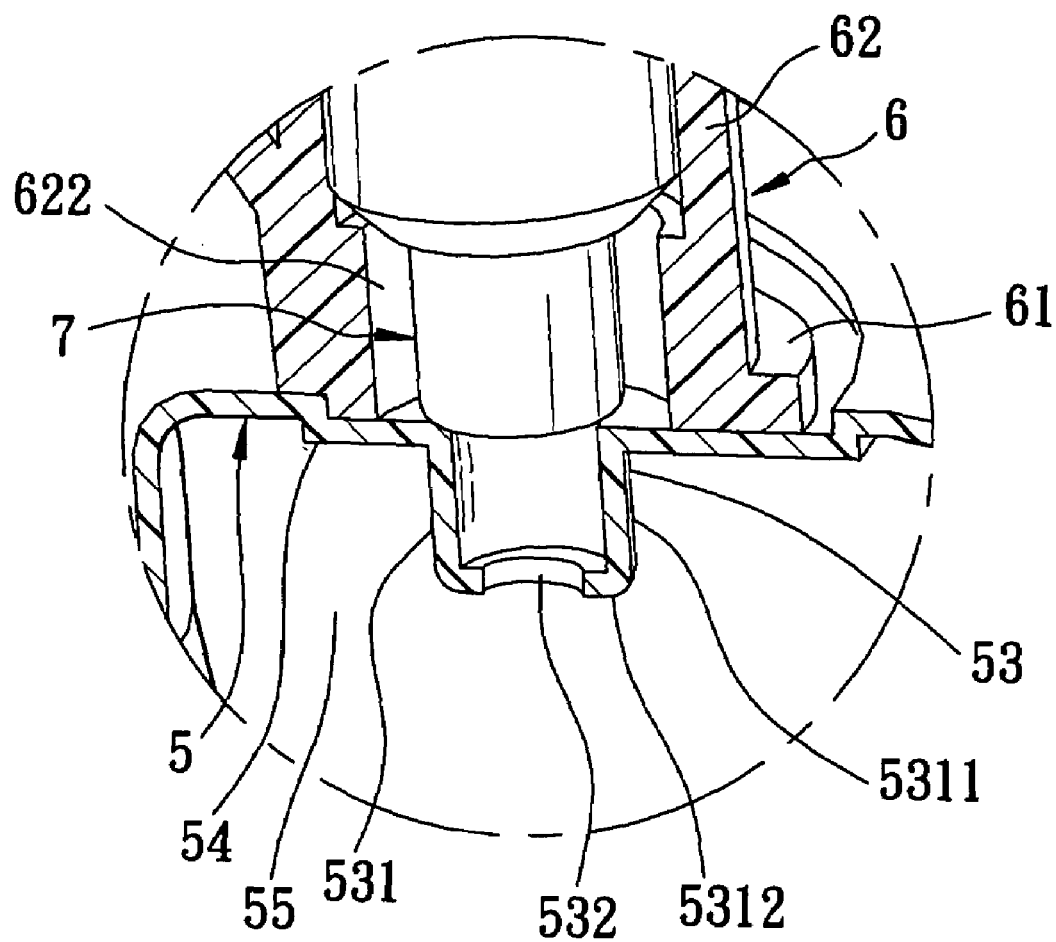
FIG. 5 is a fragmentary sectional view of the first preferred embodiment.

Referring to FIGS. 3, 4 and 5, the first preferred embodiment of a respirator mask according to this invention is shown to include an inflatable cuff 5, a gas-guiding member 6 connected to the inflatable cuff 5, and an inflating valve 7 fluidly communicating with the inflatable cuff 5.

The inflatable cuff 5 can be made by blow molding or by rotational molding. In this preferred embodiment, the inflatable cuff 5 is made by blow molding. The inflatable cuff 5 includes an inner wall surface 54 confining an air chamber 55, and a gas inlet unit 53 having a hollow protrusion 531 projecting into the air chamber 55 from the inner wall surface 54. The hollow protrusion 531 has an innermost end wall 5312 spaced apart from the inner wall surface 54, a peripheral wall 5311 extending from the inner wall surface 54 to the innermost end wall 5312, and a through hole 532 formed in the innermost end wall 5312. The hollow protrusion 531 is formed as one-piece with the inner wall surface 54. Additionally, the inflatable cuff 5 is composed of a broad mouth covering portion 51 and a tapered nose covering portion 52 connected to the broad mouth covering portion 51. In the first preferred embodiment, the gas inlet unit 53 is formed in the tapered nose covering portion 52. Alternatively, the gas inlet unit 53 can be formed in the broad mouth covering portion 51.

Figure 6:
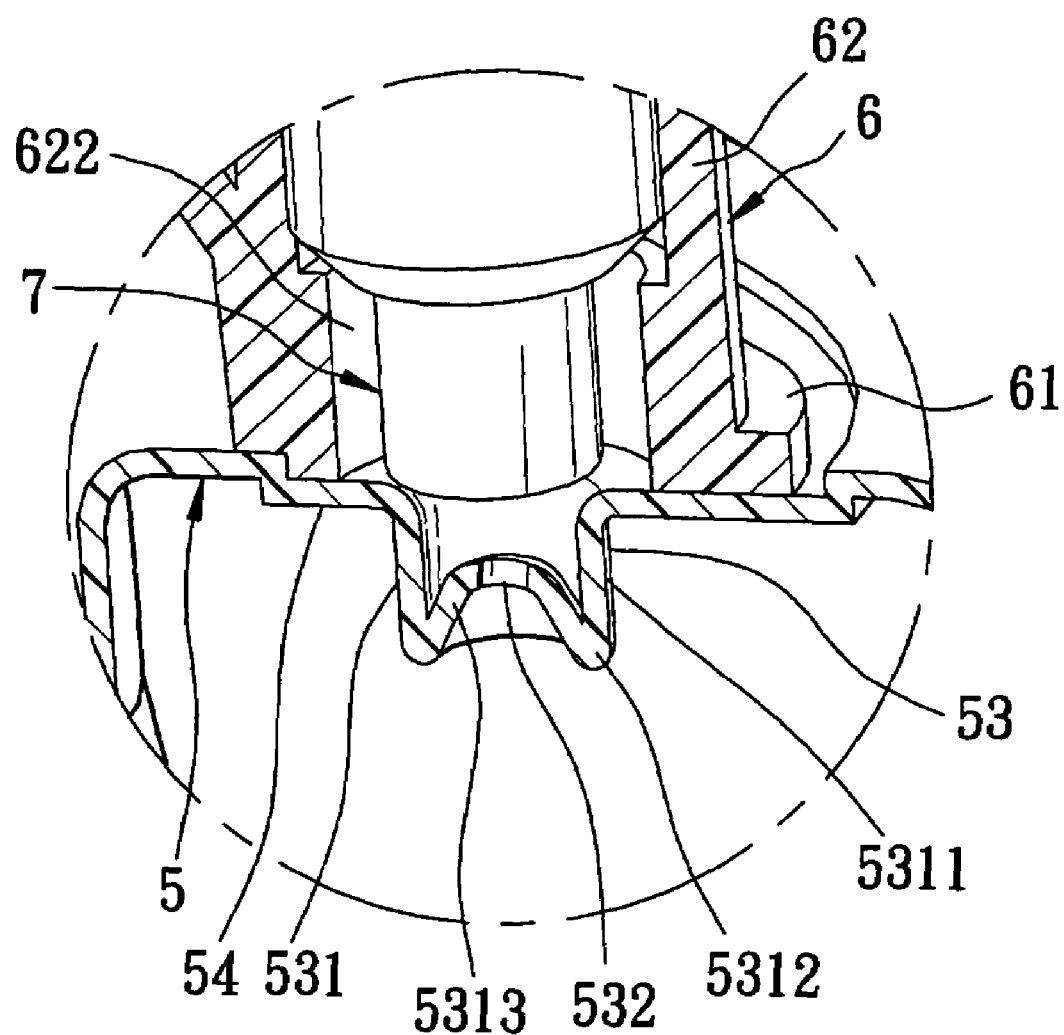
FIG. 6 is a fragmentary sectional view of a second preferred embodiment of a respirator mask according to this invention.

Referring to FIG. 6, in the second preferred embodiment, the innermost end wall 5312 can be further indented toward the inner wall surface 54 so as to form a convex flange 5313.

The gas inlet unit 53 of the inflatable cuff 5 made by blow molding or by rotational molding can have a desired small thickness. When the inflatable cuff 5 is made by blow molding, the gas inlet unit 53 can be formed simultaneously by mounting a pin corresponding to the gas inlet unit 53 in a mold for making the inflatable cuff 5 or by providing a configuration corresponding to the gas inlet unit 53 in the mold. When the inflatable cuff 5 is made by rotational molding, a pin corresponding to the gas inlet unit 53 is mounted in a mold, and the gas inlet unit 53 is formed simultaneously by rotating the mold.

The gas-guiding member 6 has an annular connecting edge portion 61 which is connected to the inflatable cuff 5 by using an adhesive and which has a hollow seat 62 aligned with the hollow protrusion 531 of the gas inlet unit 53. The gas-guiding member 6 further has a hose connecting tube 64 and a skirt member 63 extending from the annular connecting edge portion 61 to the hose connecting tube 64. The hollow seat 62 has a through hole 622 communicated with the through hole 532 of the hollow protrusion 531. The hose connecting tube 64 is used for connecting a tube (not shown) thereto so as to introduce gas, such as oxygen, into the mask via the tube for respiration of a patient.

The inflating valve 7 is mounted in the hollow seat 62, and is aligned and communicates with the through hole 532 of the hollow protrusion 531 for inflating the inflatable cuff 5 therethrough.

During fabrication, the inflatable cuff 5 is made by blow molding or by rotational molding. The gas-guiding member 6 is formed by molding, and is then connected to the inflatable cuff 5 by using the adhesive in a manner that the hollow seat 62 is aligned with the gas inlet unit 53. The through hole 532 can be formed by using a cutting tool passing through the through hole 622 of the hollow seat 62 to cut the innermost end wall 5312 of the first preferred embodiment or the convex flange 5313 of the second preferred embodiment. The inflating valve 7 is then connected to the hollow seat 62 by adhering.

Since the hollow protrusion 531 projects into the air chamber 55 from the inner wall surface 54, the through hole 532 can be formed easily by cutting without damaging the inflatable cuff 5. Furthermore, when the inflatable cuff 5 is connected to the gas-guiding member 6 by using the adhesive, while the excess adhesive may flow along the peripheral wall 5311 and some of them may flow to the innermost end wall 5312, the excess adhesive does not interfere with the forming of the through hole 532. Moreover, as shown in FIG. 6, the convex flange 5313 formed in the innermost end wall 5312 can help reduce the amount of the excess adhesive on the innermost end wall 5312.

In view of the aforesaid, the disadvantages encountered in the prior art can be overcome by the present invention.

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

I claim:

1. A respirator mask, comprising:
    an inflatable cuff including an inner wall surface confining an air chamber, and a gas inlet unit having a hollow protrusion projecting into said air chamber from said inner wall surface, said hollow protrusion having a peripheral wall projecting from said inner wall surface, and innermost end wall connected transversely to said peripheral wall opposite to said inner wall surface so that said innermost end wall is spaced apart from said inner wall surface, and a through hole formed in said innermost end wall, said through hole having a cross-section smaller than that of said hollow protrusion, said hollow protrusion being formed as one-piece with said inner wall surface;
    a gas-guiding member including an annular connecting edge portion which is connected to said inflatable cuff and which has a hollow seat aligned with said hollow protrusion, said hollow seat having a through hole communicated with through hole of said hollow protrusion; and
    an inflating valve mounted in said hollow seat.

2. The respirator mask as claimed in claim 1, wherein said gas-guiding member further includes a hose connecting tube and a skirt member extending from said annular connecting edge portion to said hose connecting tube.

3. The respirator mask as claimed in claim 1, wherein said inflatable cuff further includes a broad mouth covering portion and a tapered nose covering portion connected to said broad mouth covering portion.

4. The respirator mask as claimed in claim 3, wherein said gas inlet unit is formed in said tapered nose covering portion of said inflatable cuff.

5. The respirator mask as claimed in claim 1, wherein said innermost end wall is indented toward said inner wall surface.

* * * * *